Figure 1:
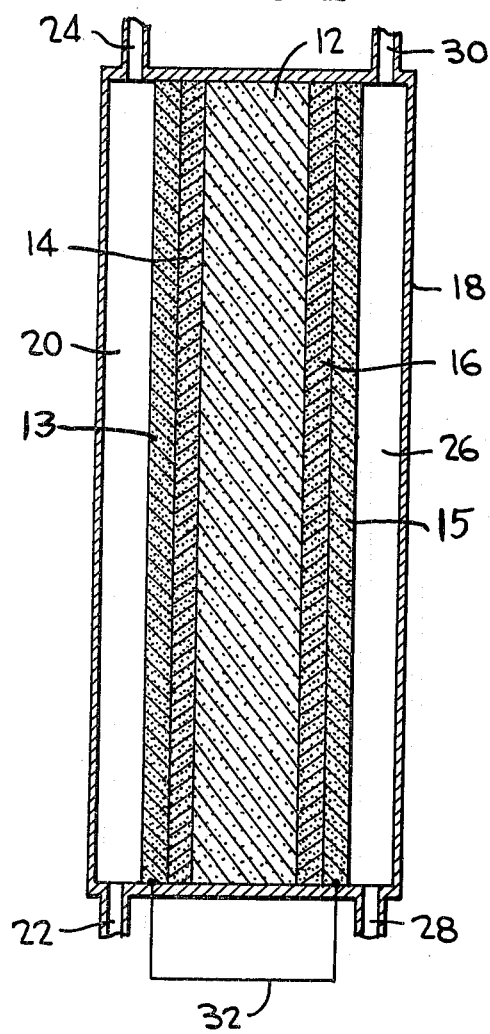

United States Patent [19]

Giner

[11] 4,167,457
[45] Sep. 11, 1979

[54] PASSIVE ELECTROLYTIC SEPARATOR

[75] Inventor: Jose D. Giner, Waltham, Mass.

[73] Assignee: Giner, Inc., Waltham, Mass.

[21] Appl. No.: 903,213

[22] Filed: May 5, 1978

[51] Int. Cl.$^2$ ............................................. G01N 27/00
[52] U.S. Cl. .................................. 204/1 T; 204/195 S
[58] Field of Search ..................... 204/1 S, 195 S, 129, 204/130

[56] References Cited

U.S. PATENT DOCUMENTS

| | | | |
|---|---|---|---|
| 3,400,054 | 9/1968 | Ruka et al. ....................... | 204/195 S |
| 3,442,773 | 5/1969 | Wilson ............................. | 204/195 S |
| 3,546,086 | 12/1970 | Sayles ............................. | 204/195 S |

Primary Examiner—R. L. Andrews
Attorney, Agent, or Firm—A. W. Breiner

[57] ABSTRACT

A device for the passive electrolytic separation of the components of a gas mixture comprising an ion-transfer medium with an anodic and cathodic surface, means for electronically short-circuiting the anodic and cathodic surfaces, and means for controlling and stabilizing the partial pressure of a gas to the anode and cathode. In operation, a gaseous mixture containing a gas which participates in a reversible electrochemical reaction at the anodic and cathodic surfaces of an electrolytic cell and inert gases are fed to the anode of the separator while the anodic and cathodic surfaces are short-circuited. The pressure of the gaseous mixture is controlled in order that the partial pressure of the gas to be separated from the mixture of gases is maintained at a higher partial pressure at the anode than at the cathode. The partial pressure differential, due to the short-circuiting of the separator, will cause the flow of the reactive gas to be separated from the anode side of the cell to the cathode side where it is recovered. The device and method provide for the passive electrolytic separation of gases with an overall high efficiency.

31 Claims, 2 Drawing Figures

PASSIVE ELECTROLYTIC SEPARATOR

The present invention is directed to a method of and a device for the electrolytic separation of the components of a gaseous mixture. More particularly, the invention is directed to a passive or auto-electrolytic gas transfer device, i.e., a gas transfer device which does not require an external driving power source.

There is a present need to develop energy sources which are dependable, not harmful to the environment, and efficient. One proposal, not totally new, is the gasification of coal. Specifically, in an oxygen-blown gasifier coal is subjected to oxygen according to the following equation:

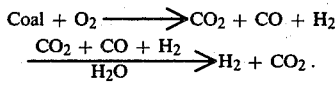

In air-blown gasifiers, in addition to $CO_2 + H_2$, the gas stream will include large amounts of nitrogen. In many applications it is necessary to separate the gaseous components of the mixture obtained. Various methods are known for gas separation including passing the gaseous mixture adjacent to a barrier such as a palladium-silver membrane selectively permeable to hydrogen; or to bring the gaseous mixture into contact with a material which will selectively adsorb carbon dioxide, such as an alkanolamine. Further, electrolytic pumps are known wherein the components of a hydrogen-carbon dioxide stream are fed to the anode of a fuel cell with pure hydrogen being transferred to the cathode of the cell for recovery.

Although all of the aforesaid methods can be successfully employed, each presents problems. For example, the palladium-silver separators as above described are expensive due to the cost and fabrication of the palladium-silver membrane. Moreover, the membranes for efficiency must be very thin and, thus, are susceptible to hole formation, permitting passage of contaminant gases. The membranes at times become poisoned due to contaminants in the gaseous mixture. The separation of carbon dioxide by contact with an alkanolamine are inefficient and require a complex system. Moreover, the systems which remove $CO_2$ from the gas stream are unable to separate nitrogen gas from the recovered hydrogen. Accordingly, with such systems it is impossible to employ air-blown gasifiers, requiring the use of gasifiers operated with pure oxygen. The electrolytic pump previously suggested, although avoiding some problems, requires an external power source to drive the fuel cell and, accordingly, the overall efficiency is again low.

OBJECTS AND GENERAL DESCRIPTION OF INVENTION

Accordingly, a primary object of the present invention is to provide a method of and apparatus for separating the components of a gaseous mixture which is safe, reliable, and efficient.

It is another object of the present invention to provide an electrolytic separator which is passive, i.e., does not require an external power source, improving its total efficiency.

The gas separator of the present invention comprises an electrolytic device which essentially is an electrolytic cell having two non-consumable electrodes, i.e., an anode and a cathode; and an ion-transfer medium separating the anode and cathode. However, unlike an electrolytic pump previously employed for the electrolytic separation of gases, the passive electrolytic separator of the present invention does not require an external power source. Rather, the electrolytic cell is short-circuited, i.e., the anode and cathode are electronically connected; and the driving force of the device is derived from a partial pressure difference maintained between or across the anode and cathode of the cell.

Although the separator of the present invention can be used, as will be considered hereinafter, to separate the components of various gaseous mixtures, including mixtures not including hydrogen, the invention for convenience will be described initially with reference to a passive electrolytic hydrogen transfer device operated in the short-circuited mode, wherein the driving force of the device is obtained from the hydrogen partial pressure difference between the anode and cathode. The magnitude of the driving force is given by the potential difference between the anode and cathode which is related to the hydrogen partial pressures by the Nernst equation:

$$\Delta E = \frac{RT}{2F} \ln \frac{P_d}{P_a}$$

where $P_d$ is the partial pressure of the hydrogen donating system (high $H_2$ partial pressure stream, or anode stream), and $P_a$ is the partial pressure of the hydrogen accepting stream (low hydrogen partial pressure stream, or cathode stream).

The rate of hydrogen transfer (per unit of area) is conventionally expressed by a current density, i, related to $\Delta E$ (and $P_d$ and $P_a$) to a first approximation by $$i = \frac{\Delta E}{r} = \frac{1}{r} \cdot \frac{RT}{2F} \ln \frac{P_d}{P_a}$$

where r is a resistance which includes ohmic resistance and electrode polarization resistance.

A partial pressure difference sufficient to obtain gas separation is obtained by operating the hydrogen donating stream at a higher absolute pressure than the hydrogen accepting stream, and/or by using an inert gas in the hydrogen accepting stream, for example a steam or nitrogen, and/or by sweeping the cathode or accepting side of the cell to provide a lower partial pressure. Specifically, a cell, at 150° C., with countercurrent gas flow with the anode entrance $H_2$ concentration being 0.75 atmospheres ($P_d$) and the cathode exit $H_2$ concentration being 0.1 atmospheres ($P_a$), the maximum potential will be 37 mV. If the anode $H_2$ concentration is allowed to drop to 0.2 atmospheres at the exit versus 0.05 atmospheres $H_2$ at the cathode entrance, the potential difference at the opposite side of the cell will be 25.6 mV. If the anode $H_2$ concentration were allowed to drop further to 0.1 atmospheres versus 0.05 atmospheres at the cathode entrance, the potential will drop to 12.8 mV at the opposite side of the cell.

The potential differences as above expressed will provide hydrogen generation at the cathode equivalent to 50–60 mA/cm² pressure using electrodes with low Pt loadings (<0.25 mg/cm²) and an acid electrolyte. The device and method of the present invention can be adjusted and modified to provide efficient separation of hydrogen from a mixture of gases including gases derived from the gasification of coal.

Although the invention has been described hereinbefore with reference to the separation of hydrogen from a gaseous mixture of hydrogen and carbon dioxide, the gas separator of the invention can also be used to separate other gases from a gaseous mixture. For example, the device and method can be utilized to separate oxygen from a mixture of oxygen and nitrogen or it can be employed to separate a mixture of chlorine from nitrogen. Effectively, the passive electrolytic separator of the invention can be used to separate any gas which participates in a reversible electrochemical reaction at the anodic and cathodic surfaces of an electrolytic cell from a gaseous mixture and where the partial pressure of the reactive gas can be controlled or stabilized to provide a driving force between the anodic and cathodic surfaces.

Although the passive electrolytic transfer device according to this invention can utilize the electrode and electrolyte matrix configurations conventionally used in a fuel cell, preferably a simplified construction will be employed. Since the two electrodes must, in fact, be short-circuited to the greatest degree possible over their entire surfaces, there is no need for electronic insulation between the electrodes, and preferably the electrodes will be in electronic contact, or a part of, the electrolytic or ion-transfer matrix. Electrolytic cell designs which can be used include:

(1) A porous, electronically conductive mat with porosity suitable to hold electrolyte, such as a graphite paper, or a non-woven mat comprising a mixture of polymeric fibers and graphite conducting fibers. Porous gas diffusion electrodes are placed on each side of the porous, conductive matrix. The electrodes can be catalytic layers which are an integral part of the porous conductive matrix. In this case most of the electronic contact is made through the matrix.

(2) A porous, electronically insulating matrix impregnated with an acid such as phosphoric acid. Teflonbonded carbon electrodes activated with small amounts of platinum are at each side of the matrix. A gas cavity is formed between each electrode and a conductive back plate or casing of the cell housing. Contact between the electrodes is made through the back plate, casing, or external wiring.

(3) A design similar to the one described in (2) but wherein the matrix is a proton conducting solid polymer electrolyte matrix, e.g., fluorinated sulfonic acid on a polystyrene backbone, or a perfluorinated sulfonic acid resin mixed with PTFE (polytetrafluoroethylene); with two thin, porous platinum electrodes placed on each side of the matrix. Contact is made as in (2) through the back plate, casing, or external wiring.

(4) A polymeric proton conducting matrix as in configuration (3) but wherein the electronic short is internal through the separator.

(5) A compact ceramic matrix which may be acid resistant and/or which may be electronically conductive. In the event chlorine is to be separated from a mixture of gases, an acid resistant matrix, such as a matrix of silica impregnated with acid, can be used. If oxygen is to be separated from a mixture of gases, an oxygen conductive matrix, such as a matrix of zirconium oxide or cerium oxide can be selected. A matrix of a material which is not acid resistant and/or electronically conductive can be rendered either acid resistant or electronically conductive by known procedures. The matrix can be short-circuited through the electronically conductive matrix or where the matrix is non-electronically conductive through external means.

The cell design as above described can be configured for stacking as conventionally done in fuel cell technology, or to be spirally wound in a configuration used in separation techniques such as ultra-filtration, blood dialysis, or the like.

DRAWING AND ILLUSTRATIVE EMBODIMENTS

Having described the invention in general terms, specific and presently preferred embodiments will be set forth in the context of the illustrative drawing.

Figure 2:
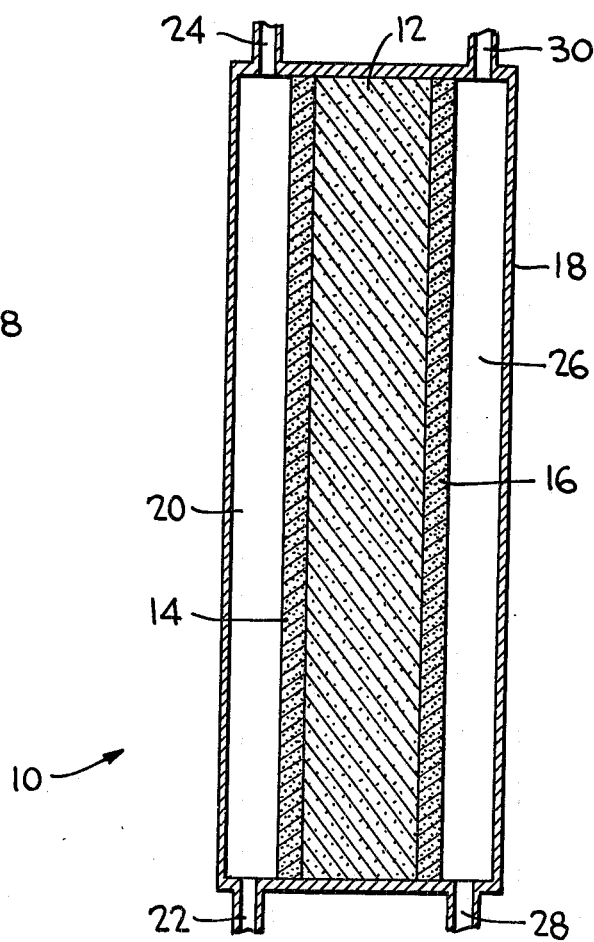

In the drawing, wherein like parts are referred to by like numbers,

FIG. 1 is a diagrammatic sectional view of a passive electrolytic separator of a first design; and FIG. 2 is a diagrammatic sectional view of a passive electrolytic separator of a preferred design.

EXAMPLE 1

A passive electrolytic separator is constructed as shown in FIG. 1 with the ion-transfer material 12 being a porous, hydrophilic graphite paper matrix. The matrix is impregnated with aqueous $H_3PO_4$. Each of anode 14 and cathode 16 comprises a mixture of polytetrafluoroethylene (PTFE) and carbon supported platinum catalyst. An electronically conducting matrix 13 and 15 of graphite fibers are positioned behind and in intimate contact with anode 14 and cathode 16, respectively. The cell housing 18 in conjunction with matrix 13 defines a gas space adjacent to the anode; and the cell housing 18 in conjunction with matrix 15 defines a gas space 26 adjacent to the cathode. The anode gas space has inlet 22 and outlet 24. The cathode gas space 26 has inlet 28 and outlet 30. Matrix 13 and matrix 15 are short-circuited through electrical lead 32.

A gaseous mixture obtained by the gasification of coal comprising hydrogen and carbon dioxide is fed into compartment 20 through inlet 22 and the cell maintained at 150° C. Gas effluent containing predominantly $CO_2$ with some $H_2$ is recovered through exit 24. The partial pressure of the hydrogen of the gas mixture at the anode is maintained at 10 atmospheres. As a result of the short-circuiting mode of the cell, hydrogen is transferred to the cathode side of the cell according to the equation as follows:

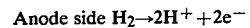

Anode side $H_2 \rightarrow 2H^+ + 2e^-$

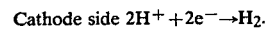

Cathode side $2H^+ + 2e^- \rightarrow H_2$.

The partial pressure on the cathode side is at 1 atmosphere maintained by sweeping the cathode side with an inert gas.

Hydrogen was recovered from outlet 30 and when analyzed contained no carbon dioxide.

EXAMPLE 2

A cell is constructed substantially as in Example 1 and as illustrated diagrammatically in FIG. 1. However, the ion-transfer matrix comprises non-porous, stabilized zirconium oxide. The matrix is ionically conductive. The anodic and cathodic surfaces are short-circuited. The cell is fed with a gaseous mixture of oxygen and nitrogen. When the cell is operated at about 1000° C., oxygen is recovered from the anode side according to the equation as follows:

Cathode side $O_2 + 4e^- \rightarrow 2O^{--}$

Anode side $2O^{--} \rightarrow O_2 + 4e^-$.

An analysis of the oxygen recovered will show no trace of nitrogen.

EXAMPLE 3

A cell is constructed substantially as in Example 1 and as illustrated in FIG. 1 with the exception that the ion-transfer matrix comprises silicon oxide impregnated with aqueous hydrochloric acid. A gaseous mixture of chlorine and nitrogen is fed to anode compartment 20. Gaseous chlorine is recovered from the anode compartment according to the equation as follows:

Cathode side $\frac{1}{2}Cl_2 + e^- \rightarrow Cl^-$

Anode side $Cl^- \rightarrow \frac{1}{2}Cl_2 + e^-$.

An analysis of the recovered chlorine will show no trace of nitrogen.

EXAMPLE 4

A passive electrolytic separator is constructed as illustrated diagrammatically in FIG. 2. The ion-transfer matrix 12 which is electronically conductive comprises graphite fibers impregnated with aqueous phosphoric acid. Anode 14 and cathode 16 are in direct contact with the electronically conductive matrix and comprise an admixture of PTFE and carbon supported platinum catalyst. As in Example 1, a gaseous mixture obtained by the gasification of coal comprising hydrogen and carbon dioxide is fed into compartment 20 through inlet 22 and the cell maintained at 120° C. The partial pressure at the anode gas space is maintained at 10 atmospheres and the partial pressure at the cathode gas space is at 1 atmosphere. The hydrogen recovered from outlet 30 when analyzed contained no carbon dioxide.

As will be apparent, in the aforesaid examples the electrodes can be modified and tailored to suit a particular application. Conventional fuel cell electrodes can be employed. Further, the matrix can be modified and tailored to meet a particular environment and application. For example, the ion-transfer matrices useful according to the invention can be constructed as matrices conventionally used in fuel cell applications. However, preferably the matrix will be electronically conductive. The electronically conductive matrix when in contact with electrodes 14 and 16 will provide the necessary short-circuiting.

As will be further apparent, it is possible to arrange the electrolytic separators in stacks as in conventional fuel cell, or gas separator construction. As will be apparent, in addition to producing pure hydrogen, the system and process can be used to enrich a gaseous stream with hydrogen for subsequent use.

It is claimed:

1. Process for the passive electrolytic separation of a gas from a mixture of gases comprising (1) providing a passive electrolytic cell including first and second electrodes, an ion-transfer material between said electrodes, and means for short-circuiting said cell; (2) feeding a mixture of gases to said first electrode of said passive electrolytic cell while maintaining said cell in the short-circuited mode; (3) maintaining a differential in the partial pressure of the gas to be separated from the gaseous mixture across said electrodes of said electrolytic cell in order that said first electrode is at a higher partial pressure than said second electrode; and (4) removing the gas to be separated from said cell.

2. The process of claim 1 wherein the mixture of gases fed to said first electrode is a mixture of hydrogen and carbon dioxide, and the gas to be recovered is hydrogen.

3. The process of claim 2 wherein the electrolytic cell comprises at least one electrode which includes a mixture of platinum and polytetrafluoroethylene (PTFE), and the ion-transfer material is a conductive carbon matrix impregnated with an acid electrolyte.

4. The process of claim 3 wherein the acid is phosphoric acid.

5. The process of claim 4 wherein the electrodes are each an admixture of PTFE and porous carbon activated with platinum.

6. The process of claim 1 wherein the gaseous mixture includes chlorine and the gas to be separated is chlorine.

7. The process of claim 6 wherein the ion-transfer material is an acid resistant matrix.

8. The process of claim 7 wherein said acid resistant matrix includes silica.

9. The process of claim 8 wherein the acid resistant matrix is electronically conductive.

10. The process of claim 1 wherein the mixture of gases includes oxygen and nitrogen; the gas to be separated is oxygen, and the ion-transfer material of the electrolyte is an oxygen ion-conductive ceramic matrix.

11. The process of claim 10 wherein the oxygen ion-conductive ceramic matrix includes zirconium oxide.

12. The process of claim 10 wherein the oxygen ion-conductive ceramic includes ceric oxide.

13. The process of claim 10 wherein the oxygen ion-conductive matrix is electronically conductive.

14. The process of claim 1 wherein the partial pressure differential is maintained by controlling the partial pressure across said electrodes of said cell to provide a high partial pressure at said first electrode and a low partial pressure at said second electrode.

15. The process of claim 1 wherein the partial pressure differential is maintained by diluting the gas to be separated with a condensible inert gas.

16. The process of claim 1 wherein the partial pressure differential is maintained by sweeping the separated gas from said second electrode surface.

17. The process of claim 1 wherein said electrodes are integral with the ion-transfer material.

18. A passive electrolytic separator comprising an electrolytic cell including first and second electrodes, an ion-transfer material between said electrodes, means for electronically connecting said electrodes to short-circuit said cell, and means for feeding a gaseous mixture to said first electrode and means for removing a gaseous stream from said second electrode, said means for feeding a gaseous mixture and said means for removing a gaseous stream including means for maintaining a partial pressure differential between said electrodes.

19. The electrolytic separator of claim 18 wherein the ion-transfer material comprises a porous matrix.

20. The electrolytic separator of claim 19 wherein the matrix is an acid resistant matrix.

21. The electrolytic separator of claim 20 wherein the acid resistant matrix includes silica.

22. The electrolytic separator of claim 21 wherein the matrix is impregnated with aqueous hydrochloric acid.

23. The electrolytic separator of claim 22 wherein the matrix is electronically conductive.

24. The electrolytic separator of claim 19 wherein the matrix is oxygen ion-conductive.

25. The electrolytic separator of claim 24 wherein the oxygen ion-conductive matrix includes zirconium oxide.

26. The electrolytic separator of claim 24 wherein the oxygen ion-conductive matrix includes ceric oxide.

27. The electrolytic separator of claim 24 wherein the matrix is electronically conductive.

28. The electrolytic separator of claim 19 wherein at least one of said electrodes is integral with said matrix.

29. The electrolytic separator of claim 28 wherein the matrix comprises graphite fibers, and said electrodes each comprises a mixture of PTFE and carbon supported platinum.

30. The electrolytic separator of claim 19 wherein the matrix comprises conductive graphite fibers.

31. The electrolytic separator of claim 18 wherein said means for electronically connecting said electrodes is an electronically conductive ion-transfer material in direct electronic contact with each of said electrodes.

* * * * *